(12) United States Patent
Fusari

(10) Patent No.: US 7,925,664 B2
(45) Date of Patent: *Apr. 12, 2011

(54) METHODS AND APPARATUS FOR MANAGING USER ACCESS TO A COMPUTING ENVIRONMENT

(75) Inventor: David Fusari, Groton, MA (US)

(73) Assignee: Sentillion, Inc., Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/645,103

(22) Filed: Dec. 22, 2009

(65) Prior Publication Data

US 2010/0100956 A1 Apr. 22, 2010

Related U.S. Application Data

(63) Continuation of application No. 11/497,854, filed on Aug. 1, 2006, now Pat. No. 7,647,324.

(51) Int. Cl.
G06F 17/30 (2006.01)

(52) U.S. Cl. .................................................. 707/770

(58) Field of Classification Search .................. 707/609, 707/705, 736, 770, 781, 802, E17.117, E17.119; 709/217, 227; 713/186; 726/22
See application file for complete search history.

(56) References Cited

U.S. PATENT DOCUMENTS

| 5,960,085 | A | 9/1999 | De La Huerga |
| 6,857,021 | B1 | 2/2005 | Schuster et al. |
| 7,076,083 | B2 | 7/2006 | Blazey |
| 2003/0084287 | A1 | 5/2003 | Wang et al. |
| 2004/0230809 | A1 | 11/2004 | Lowensohn et al. |
| 2005/0091338 | A1* | 4/2005 | de la Huerga ............. 709/217 |
| 2006/0090079 | A1* | 4/2006 | Oh et al. ...................... 713/186 |
| 2007/0136792 | A1 | 6/2007 | Ting et al. |
| 2008/0109895 | A1 | 5/2008 | Janevski |

OTHER PUBLICATIONS

International Search Report from corresponding application PCT/US2007/017066 filed Jul. 31, 2007.
Itoi, "Smartcard Integration with kerberos V5", CITI Technical Report 98-7, Dec. 3, 1998, pp. 1-11, Center for Information Technology Integration, USA.
International Preliminary Report on Patentability, dated Oct. 16, 2008.

* cited by examiner

Primary Examiner — Fred I Ehichioya
(74) Attorney, Agent, or Firm — Wolf, Greenfield & Sacks, P.C.

(57) ABSTRACT

Methods and apparatus for controlling user access to a computing environment are provided. In one embodiment, a method performed by a user is provided for gaining access to at least one computing device. The method comprises gaining access to the at least one computing device at a first time by providing credential information to the at least one computing device to authenticate the user's identity to the at least one computing device; presenting to the at least one computing device a physical device comprising identifying information to associate the physical device with the user authenticated by the credential information; and gaining access to the at least one 10 computing device at a subsequent time by presenting the physical device to the at least one computing device without providing the credential information.

11 Claims, 4 Drawing Sheets

METHODS AND APPARATUS FOR MANAGING USER ACCESS TO A COMPUTING ENVIRONMENT

RELATED APPLICATIONS

This application is a continuation of U.S. application Ser. No. 11/497,854, entitled "METHODS AND APPARATUS FOR MANAGING USER ACCESS TO A COMPUTING ENVIRONMENT," filed on Aug. 1, 2006, which is incorporated by reference herein in its entirety.

FIELD OF INVENTION

This invention relates generally to controlling user access to one or more computing devices.

BACKGROUND OF INVENTION

In many computing environments, a user must authenticate (i.e., prove) his or her identity to gain access to one or more computing devices. For example, a user may be required to provide information (such as a user identifier (ID) and password) and/or a biometric (e.g., fingerprint, retinal scan, etc.) to gain access to a workstation. Only after being authenticated may the user be given access to one or more applications on the workstation and the data accessible thereby. Thus, one concern addressed via user authentication is the security of those applications and data.

In some environments, the applications and/or data may include sensitive information. For example, patient privacy is a concern in healthcare settings. For example, the Health Information Portability and Accountability Act (HIPAA) mandates that only certain authorized users be given access to certain clinical information relating to a given patient. As a result, many healthcare organizations forbid users from sharing authentication information (such as user identifiers and/or passwords) so that the organization can ensure that each user provides his or her own authentication information to gain access to a computing device.

SUMMARY OF INVENTION

One embodiment of the present invention provides a method for authenticating a user to a computing device. In one embodiment, the method is performed by a user, and comprises acts of: (A) gaining access to at least one computing device at a first time by providing credential information to the at least one computing device to authenticate the user's identity to the at least one computing device; (B) presenting to the at least one computing device a physical device comprising identifying information to associate the physical device with the user authenticated by the credential information; and (C) gaining access to the at least one computing device at a second time, subsequent to the first time, by presenting the physical device to the at least one computing device without providing the credential information to authenticate the user's identity to the at least one computing device at the second time.

Another embodiment provides a method of controlling access to at least one computing device. The method comprises acts of: (A) in response to a user seeking access to the at least one computing device by presenting a physical device comprising identifying information, determining whether the physical device was previously associated with a user who, within a grace period of time, accessed the at least one computing device as a result of the user having provided credential information to the at least one computing device to authenticate the user's identity and who presented the physical device to the at least one computing device to associate the physical device with the user identified by the credential information; (B) when it is determined in the act (A) that the physical device was not previously associated with a user who, within the grace period of time, accessed the at least one computing device as a result of the user having provided the credential information to the at least one computing device to authenticate the user's identity and who presented the physical device to the at least one computing device to associate the physical device with the user identified by the credential information, requiring that to gain access to the at least one computing device the user provide the credential information to the at least one computing device to authenticate the user's identity; and (C) when it is determined in the act (A) that the physical device was previously associated with a user who, within the grace period of time, accessed the at least one computing device as a result of the user having provided the credential information to the at least one computing device to authenticate the user's identity and who presented the physical device to the at least one computing device to associate the physical device with the user identified by the credential information, enabling the user to gain access to the at least one computing device by presenting the physical device to the at least one computing device without requiring the user to provide the credential information to the at least one computing device to authenticate the user's identity.

Yet another embodiment of the invention provides at least one computer readable medium encoded with a plurality of instructions that, when executed, perform a method of controlling access to at least one computing device. The method comprises acts of: (A) in response to a user seeking access to the at least one computing device by presenting a physical device comprising identifying information, determining whether the physical device was previously associated with a user who, within a grace period of time, accessed the at least one computing device as a result of the user having provided credential information to the at least one computing device to authenticate the user's identity and who presented the physical device to the at least one computing device to associate the physical device with the user identified by the credential information; (B) when it is determined in the act (A) that the physical device was not previously associated with a user who, within the grace period of time, accessed the at least one computing device as a result of the user having provided the credential information to the at least one computing device to authenticate the user's identity and who presented the physical device to the at least one computing device to associate the physical device with the user identified by the credential information, requiring that to gain access to the at least one computing device the user provide the credential information to the at least one computing device to authenticate the user's identity; and (C) when it is determined in the act (A) that the physical device was previously associated with a user who, within the grace period of time, accessed the at least one computing device as a result of the user having provided the credential information to the at least one computing device to authenticate the user's identity and who presented the physical-device to the at least one computing device to associate the physical device with the user identified by the credential information, enabling the user to gain access to the at least one computing device by presenting the physical device to the at least one computing device without requiring the user to provide the credential information to the at least one computing device to authenticate the user's identity.

Yet another embodiment of the invention provides a computer system comprising: at least one processor programmed to control access to computer system, wherein in response to a user seeking access to the at least one computer system by presenting a physical device comprising identifying information, the at least one processor is programmed to: determine whether the physical device was previously associated with a user who, within a grace period of time, accessed the at least one computer system as a result of the user having provided credential information to the at least one computer system to authenticate the user's identity and who presented the physical device to the at least one computer system to associate the physical device with the user identified by the credential information; require that to gain access to the at least one computer system the user provide the credential information to the at least one computer system to authenticate the user's identity when the at least one processor determines that the physical device was not previously associated with a user who, within the grace period of time, accessed the at least one computer system as a result of the user having provided the credential information to the at least one computer system to authenticate the user's identity and who presented the physical device to the at least one computer system to associate the physical device with the user identified by the credential information; and enable the user to gain access to the at least one computer system by presenting the physical device to the at least one computer system without requiring the user to provide the credential information to the at least one computer system to authenticate the user's identity when the at least one processor determines that the physical device was previously associated with a user who, within the grace period of time, accessed the at least one computer system as a result of the user having provided the credential information to the at least one computer system to authenticate the user's identity and who presented the physical device to the at least one computer system to associate the physical device with the user identified by the credential information.

BRIEF DESCRIPTION OF DRAWINGS

The accompanying drawings are not intended to be drawn to scale. In the drawings, each identical or nearly identical component illustrated in the various figures is represented by a like numeral. For purposes of clarity, not every component may be labeled in every drawing. In the drawings.

DETAILED DESCRIPTION

Figure 1:
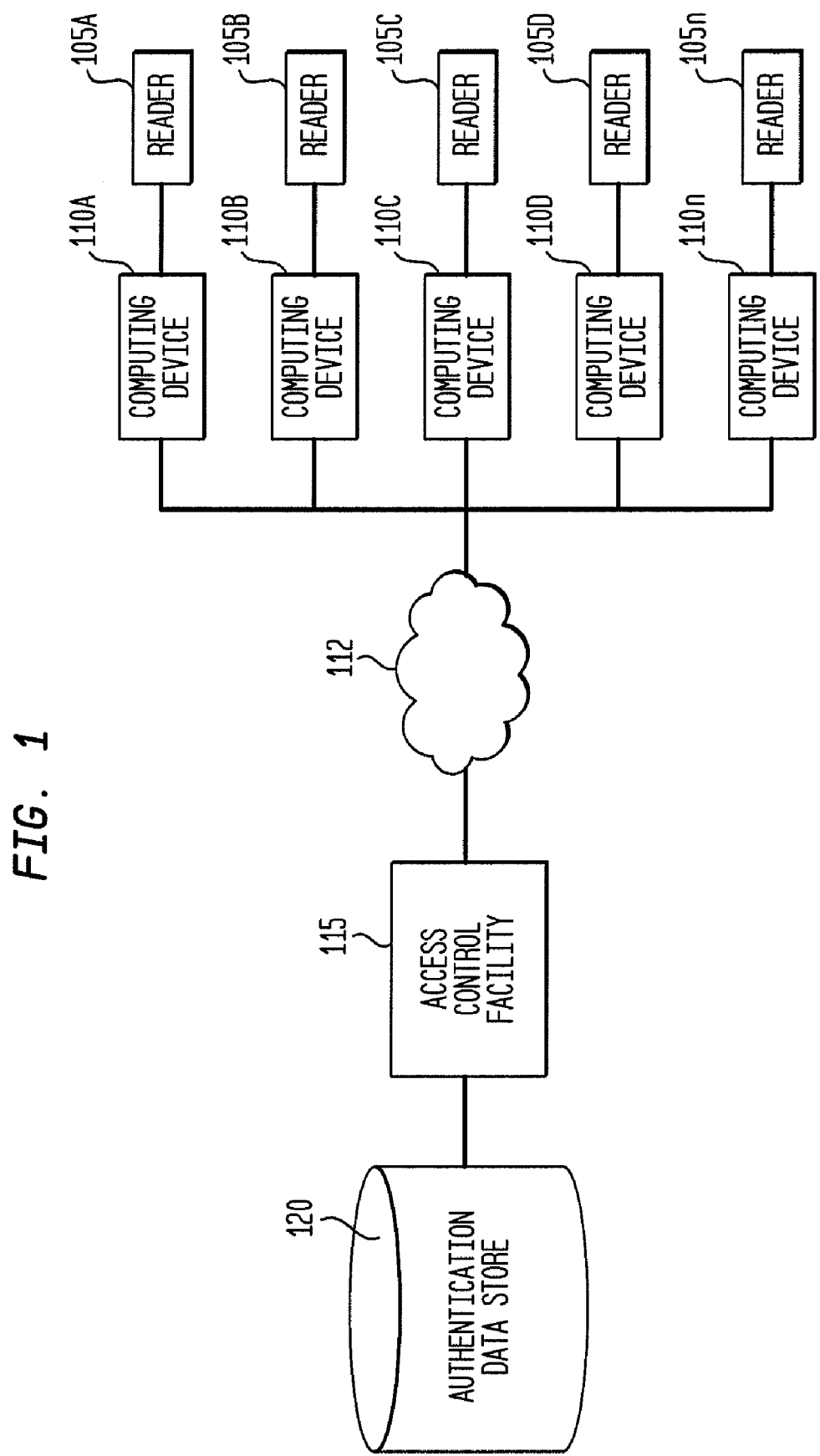
FIG. 1 is a block diagram depicting one example of a system for authenticating users, in accordance with one embodiment of the invention.

Applicants have appreciated that in some computing environments it may be desirable to minimize the intrusiveness or disruptiveness of requiring a user to engage in the authentication process each time the user accesses the computing environment. One example of such an environment is a healthcare organization, wherein healthcare providers (e.g., doctors and nurses) often share access to a networked computing environment through one or more shared workstations. During the course of a workday, a healthcare provider may seek access to the network through multiple different workstations numerous times throughout the day. As it is desirable to enable healthcare providers to quickly and easily access applications and data to facilitate effective administration of care to patients, applicants have appreciated that it is desirable to minimize the time and effort needed to gain access to the computing environment.

In accordance with one embodiment of the present invention, a system is provided that enables a user to initially gain access to a computing environment by providing credential information (e.g., a user ID and password, biometric information, etc.), and in association with that access the user may also present to the computing device a physical device that includes identifying information so that the computing device can associate the authenticated user with the physical device. Subsequently, the user may gain access to the computing device by simply presenting the physical device without the necessity of again providing the credential information to authenticate the user's identity. Thus, the second access can be accomplished more quickly and easily.

In accordance with one embodiment of the present invention, the computing system only accepts the presentation of the physical device (without credential information) during a specified grace period after the user is authenticated by providing credential information, so that after the expiration of the grace period, the user must again provide authenticating credential information to be granted access to the computing environment. In this respect, applicants have appreciated that security concerns could be raised without the imposition of a grace period, as the physical device could be lost or stolen from the rightful owner. Thus, by establishing a desired grace period, the convenience of providing access solely with the physical device can be balanced with security concerns and tailored to a particular environment. Where security concerns are particularly important, the grace period can be selected to be short to minimize the likelihood of the physical device being used within the grace period after being stolen from or lost by the rightful user.

While a networked computing environment comprising one or more shared workstations in a healthcare setting is described herein as one application for the disclosed aspects of the present invention, it should be appreciated that the embodiments of the present invention described herein are not limited to use in a healthcare environment, use with a networked computing environment, and/or use in a shared workstation environment, as the aspects of the present invention described herein can be used with any computing environment. Access to the computing environment can be obtained through any type of computing device (e.g., a workstation, personal computer, personal digital assistant (PDA), cellular telephone, and/or any other type of computing device), as the aspects of the invention described herein are not limited in this respect.

Similarly, the embodiments of the present invention described herein are not limited in any way by the particular type of physical device that may be used to gain access to the computing environment after the user has been authenticated, as any suitable type of physical device can be employed. In accordance with one embodiment of the present invention, an access badge of the type employed by numerous organizations to control access to areas of a facility is employed so that users who already possess such an access badge need not be equipped with an additional physical device. However, the invention is not limited in this respect, as other types of physical devices can be employed.

An access badge works by supplying to a badge reader (e.g., via a radio frequency) information associated with the user to whom the badge is issued. When the badge is within range of a reader, the reader interprets the information stored thereon, determines whether the user associated with the badge should be granted access to the area controlled by the card reader (e.g., by performing a lookup of a database of user identifiers), and grants or denies access as appropriate.

Access badges may be active or passive proximity badges. An active badge includes its own power source and is capable of providing information to a reader at relatively large distances. As a result, users of active badges usually are not required to affirmatively present the badge to a reader to gain access. Conversely, a passive proximity badge does not include its own power source, but rather is powered by a reader when it gets within range. As such, passive proximity badges generally have a much shorter range than active proximity badges, and require that the user affirmatively place the badge near a reader (usually within a few inches) for the badge to be read.

In accordance with one embodiment of the present invention, a passive proximity badge is employed as the physical device which can be used to gain access after the user has been authenticated. A passive proximity badge is desirable because, as discussed above, many organizations already require use of some type of access badge, so that the user would not be required to have any additional physical device to employ aspects of the present invention described herein. In addition, a passive proximity badge provides advantages over an active badge, in that a passive proximity badge requires an affirmative gesture from a user to be read. This provides relatively increased security as opposed to an active badge which could trigger a computing device to provide access to the user in the vicinity even if the user did not intend to access the computing device and may be unaware of the granted access, thereby providing an opportunity for another unauthorized user to take advantage of the granted access. Although a passive proximity badge provides some benefits, it should be appreciated that the invention is not limited in this respect, and that embodiments of the present invention can alternatively be practiced employing an active access badge or any other suitable type of physical device.

As discussed above, in accordance with one embodiment of the invention, credential information is initially presented to authenticate the user. The aspects of the present invention described herein are not limited in any respect by the nature of the credential information, as any suitable type can be employed (e.g., a user ID and password, biometric information, and/or any other suitable credential information). A physical device (e.g., a passive proximity badge) can then be associated with the authenticated user. The association can be performed in any suitable manner, as the aspects of the present invention described herein are not limited in this respect. For example, the physical device may be presented to the computing device as the user provides the credential information, or it may be presented to the computing device at any time during the pendency of a session on the computing device wherein the user was authenticated using credential information. Once the physical device has been associated with the authenticated user, the user may subsequently gain access to the computing environment (e.g., using the same computing device as the one on which the user was initially authenticated or a different device) by presenting the physical device only, without the need to re-present credential information.

As discussed above, in accordance with one embodiment of the present invention a grace period is established during which time the physical device can be employed to after the user has been authenticated without re-supplying credential information. When a grace period is established, a user presenting only the physical device after the expiration of the grace period will be denied access.

In one embodiment, the user may also, or alternatively, be assigned a "grace count" which establishes a maximum number of times that the user may be granted access to the computing environment using only the physical device (i.e., without also supplying credential information).

The grace period and/or grace count may be established based upon any suitable criteria, examples of which include the sensitivity of the information to which the user has access (e.g., with a shorter grace period for users having access to particularly sensitive information), the user's position or role in an organization (e.g., a physician versus a nurse), the particular department in the organization that the user belongs to, etc. In one embodiment, the grace period and/or grace count may be configurable.

As discussed above, embodiments of the invention may be implemented in a healthcare facility. The following example illustrates how one embodiment of the invention may be implemented in a hospital. A doctor may log into a hospital network workstation at 8:00 a.m. To do so, the doctor places her passive proximity badge in range of a reader in communication with the workstation. The reader reads information identifying the doctor from the badge and may supply this information to the workstation. The workstation may (optionally) initiate a lookup (e.g., of a database of user authentication information) using the information supplied by the badge and present an authentication interface (e.g., a log-in screen) to the user. The interface may, for example, be pre-populated with the user's ID (e.g., returned from the lookup). The doctor may then supply the remainder of the credential information to the authentication interface, such as a password and/or other credential information. If the doctor is successfully authenticated based on the credential information, she is granted access to the workstation. An indication may be recorded (e.g., in a database) that the doctor was fully authenticated (i.e., provided credential information) and associated with her badge at 8:00 a.m. The fact that the information on her badge and her credential information were both provided during the same session at the workstation establishes that she was then in possession of the badge. When the doctor completes her session on the workstation she may end it by closing out the session (e.g., by logging out).

Later, the doctor may attempt a second access of the hospital computing network (e.g., through the same or another workstation). To do so, she may place her badge in range of a reader in communication with the workstation. The reader may read the information provided by the badge and provide it to the workstation, which initiates a determination (e.g., performed by a software facility executing on the workstation or one or more other computing devices in the network) of when the doctor was last fully authenticated and whether the last full authentication was within her grace period. For example, if the doctor's grace period is four hours and the doctor's second access attempt occurs at 8:30 a.m., it will be determined that because her last full authentication was less than four hours ago, she is within her grace period, and she will be granted access to the computer without having to re-supply credential information. However, if the doctor's second access attempt occurs at 1:00 p.m., it will be determined that because her last authentication was more than four hours ago, she is not within her grace period. If so, the workstation would require the doctor to again authenticate her identity by supplying credential information. If the doctor does so and associates her badge with that authenticated session (e.g., by presenting the badge to the reader at login or during the session), a new grace period may be started for her.

It should be appreciated that the example above is provided merely for illustrative purposes and that the aspects of the present invention are not limited to a system that operates in precisely the manner described above. As mentioned, the physical device is not limited to a passive proximity badge, as other types of devices can be employed. As other examples, the system is not limited to requiring that the physical device be provided at the beginning of a login session, as the presentation can occur at any time prior to the user ending the session, and the system is not limited to pre-populating an authentication interface based upon information obtained from the physical device.

One example of a computing environment (e.g., system 100) on which aspects of the present invention can be implemented is shown in FIG. 1. System 100 comprises a computing environment including a plurality of computing devices 110A-110n in communication via a network 112. The computing environment may be implemented in a healthcare environment, or any other suitable environment.

System 100 includes an access control facility 115 in communication with an authentication datastore (e.g., database 120). The access control facility 115 and authentication datastore 120 are described further below. Each computing device 110 is in communication with a corresponding reader 105. For example, computing device 110A communicates with reader 105A.

In one embodiment, when a user presents a physical device (e.g., a passive proximity badge (not shown) or other suitable device) to a reader 105 (e.g., reader 105B), the reader reads information from the physical device and supplies it to the corresponding computing device 110 (e.g., computing device 110B), which, as described above, may comprise any suitable computing device, such as a workstation, personal computer, PDA, cellular telephone, other computing device or combination thereof. The computing device then communicates the information (e.g., via network 112 which may include any suitable networking infrastructure that facilitates communication via any suitable protocol as the invention is not limited in this respect) to access control facility 115.

In one embodiment, the access control facility 115 includes one or more components designed to process the information provided by the physical device to control access by the user to the system 100. Access control facility 115 may include any suitable number of software, hardware and/or firmware components designed to process the information supplied by the physical device, and may be implemented and/or execute on any suitable number of computing devices. For example, in one embodiment, access control facility 115 includes a plurality of software modules which execute on a single server computer. Alternatively, the access control facility 115 can be implemented in a distributed fashion among two or more computers. The access control facility may be implemented on one or more of the computing devices through which the user(s) gain access to the computing environment or on one or more other computers.

In the illustrative system 100, the access control facility 115 is coupled to the computing devices 110 via a network 112. However, it should be appreciated that the present invention is not limited to use in a networked computing environment, as the access control facility 115 can be connected to the computing devices 110 in any suitable manner. In addition, it should be appreciated that the aspects of the present invention described herein are not limited to use in a system comprising a plurality of different computing devices to which access can be granted, and can be employed to control access to even a single computing device.

It should be appreciated that a reader 105 need not be coupled directly to the computing device 110 to which it controls access. For example, a reader may be positioned in a physical location near a computing device but need not be coupled directly to it. The invention is not limited to use on a computer system having any particular hardware implementation.

Using the information provided by the physical device, access control facility 115 may initiate a lookup, based at least in part on this information, of the authentication datastore 120, which in one embodiment stores information relating to user authentication. For example, authentication datastore 120 may store credential information or derivations thereof (e.g., user IDs and passwords, biometric information, etc.); information on past authentication activity (e.g., when each user was last authenticated, whether a physical device was associated with the user during the last authenticated session, a history of past user access, etc.); information relating to user access privileges, grace periods, and grace counts; and/or any other suitable information. Authentication datastore 120 may be implemented as any suitable number of data structures, stored on any suitable number of computers, storing information in any suitable manner, and need not be organized in any particular way. In one embodiment, authentication datastore 120 is implemented as a relational database residing on the same server as access control facility 115. However, the invention is not limited to any particular implementation.

In response to the lookup, authentication datastore 120 may provide results to access control facility 115, which in turn may process the results and communicate instructions, via network 112, to the computing device 110 corresponding to the reader 105 to which the user presented the physical device. For example, after receiving lookup results that include an indication of a user's last authenticated access and grace period, access control facility 115 may process the results to determine that the user has not had an authenticated access associated with the physical device during the grace period, and issue instructions to computing device 110 to require the user to supply credential information to authenticate the user's identity. As discussed above, in one embodiment of the invention, the computing device 110 may process the instructions and present an authentication interface to the user (e.g., a login screen) to assist the user in supplying credential information, although the invention is not limited in this respect.

Access control facility 115 may issue any suitable instructions to a computing device 110, and these instructions may be processed by the computing device in any suitable manner, as this embodiment of the invention is not limited to being implemented in any particular way.

Figure 2B:
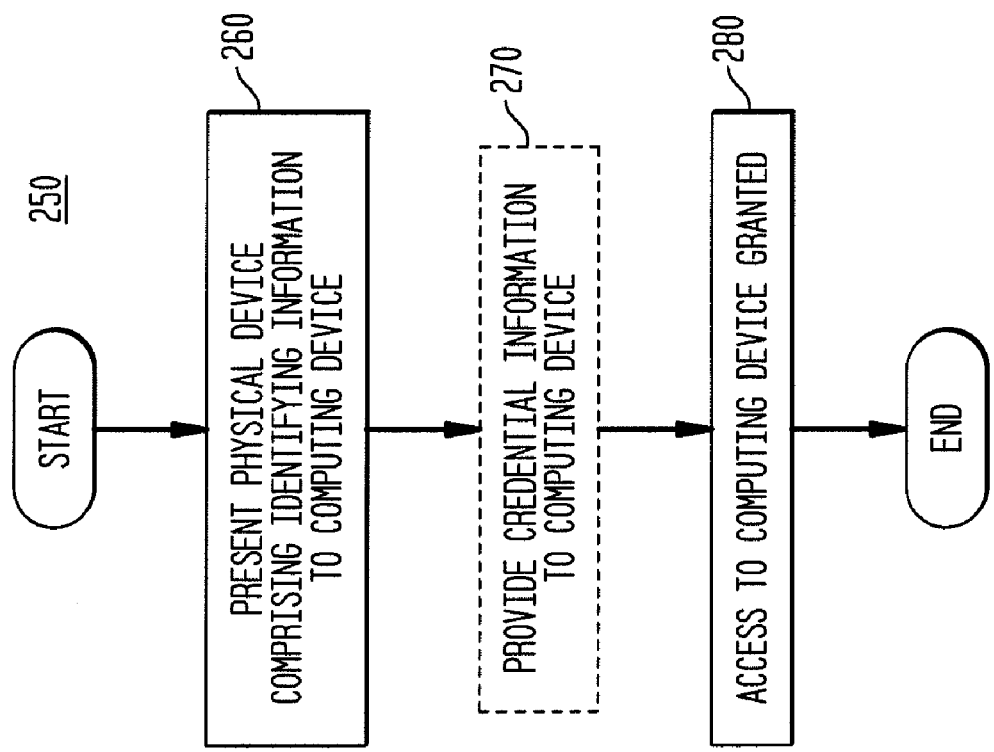
FIGS. 2A and 2B are flowcharts depicting a process whereby a user may be granted access to at least one computing device at first and second times, respectively, in accordance with one embodiment of the invention.
Figure 2A:
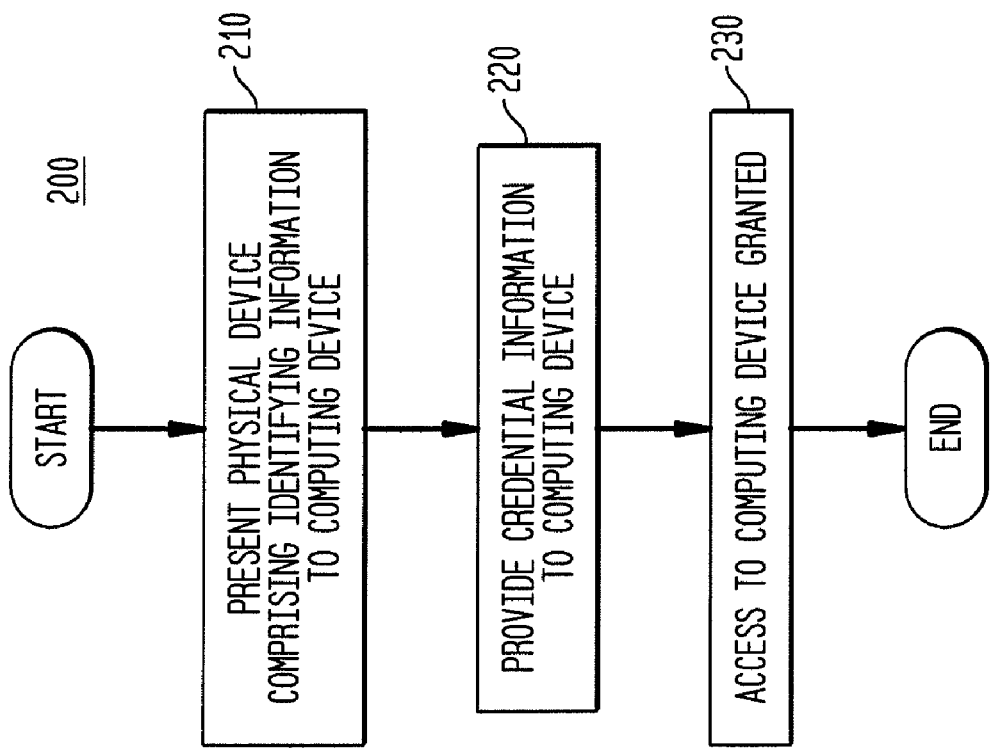

FIGS. 2A and 2B illustrate two processes that a user may perform to gain access to a computing environment in accordance with one embodiment of the invention. Initially, in process 200 (FIG. 2A) the user presents a physical device comprising information identifying the user to a computing device (e.g., computing device 110, FIG. 1) in act 210. For example, the user may present a passive proximity badge or any other suitable physical device to a reader (e.g., reader 105) in communication with the computing device. The physical device may include any suitable identifying information which the reader may read and provide to the computing device.

In act 220, the user provides credential information to the computing device. This can be performed in any suitable way. For example, when the reader communicates the identifying information to the computing device, the computing device may present an authentication interface (e.g., a login screen) that has some of the credential information filled in (e.g., a user name or ID) and prompts the user to provide the remainder of the credential information (e.g., a password). Thus, based on the identifying information provided by the badge reader in act 210, the computing device may initiate a process whereby the user is preliminarily identified (e.g., via a lookup of authentication datastore 120 using the identifying information), such that the authentication interface is pre-populated with information relating to the user (e.g., the user ID).

After the credential information is provided, the process proceeds to act 230, wherein the user is granted access to the computing device.

In the embodiment described above, the credential information provided in act 220 is a user ID and password. However, as discussed above, the aspects of the present invention described herein are not limited in this respect, as the credential information to can take any suitable form, including biometric information (e.g., a fingerprint or retina scan) or any other suitable information.

Similarly, in the illustrative embodiment shown in FIG. 2A, the physical device is presented to the computing device prior to the user providing credential information, and a portion of the credential information is automatically obtained from the physical device. However, it should be appreciated that the invention is not limited in this respect, and that the computing device need not automatically obtain any of the credential information from the physical device. In addition, it is not necessary that the physical device be provided prior to the user providing credential information, as the physical device alternatively can be provided simultaneously with the user providing credential information, or after the user has provided the credential information. In this respect, one purpose for the user providing the physical device is to demonstrate that the user is in possession of it at the time the user provided the credential information. Thus, the user can provide the physical device to the computing device at any time during a user session of the computing device during which the user provided the credential information. For example, in accordance with one embodiment of the present invention, a user can provide the credential information to gain access to the computing device, and at any time prior to terminating the session, the user may provide the physical device to associate the physical device with the user.

As discussed above, when the user presents the physical device to the computing device in association with a session during which the user has provided credential information, the computing system may record an indication that the user has been authenticated and was in possession of the physical device at that time. This recordation can be implemented in any suitable manner, as discussed above.

Process 250 (FIG. 2B) is performed when the user attempts to access the computing environment at a subsequent time (e.g., after termination of the user session begun by the process 200 of FIG. 2A). At the start of the process 250, the user presents the physical device comprising identifying information to a computing device of the computing environment in act 260. This computing device may be the same computing device the user accessed in act 230 or another. As described above with reference to act 210, the physical device presented may be a passive proximity badge or any other suitable physical device, and it may be presented to a reader which is in communication with the computing device.

The next action required by the user depends upon the manner in which the computing environment responds to the presentation of the physical device, as illustrated by the dotted act 270. Specifically, depending upon various factors that the computer environment may consider as discussed below (e.g., whether the user's grace period has expired), the user may simply be granted access to the computing device in act 280. Alternatively, if the computing environment determines, based on its evaluation factors, that the user will not be granted access based solely on the presentation of the physical device, the user may be prompted to provide credential information in act 270 prior to being granted access to the computing device in act 280.

Figure 3:
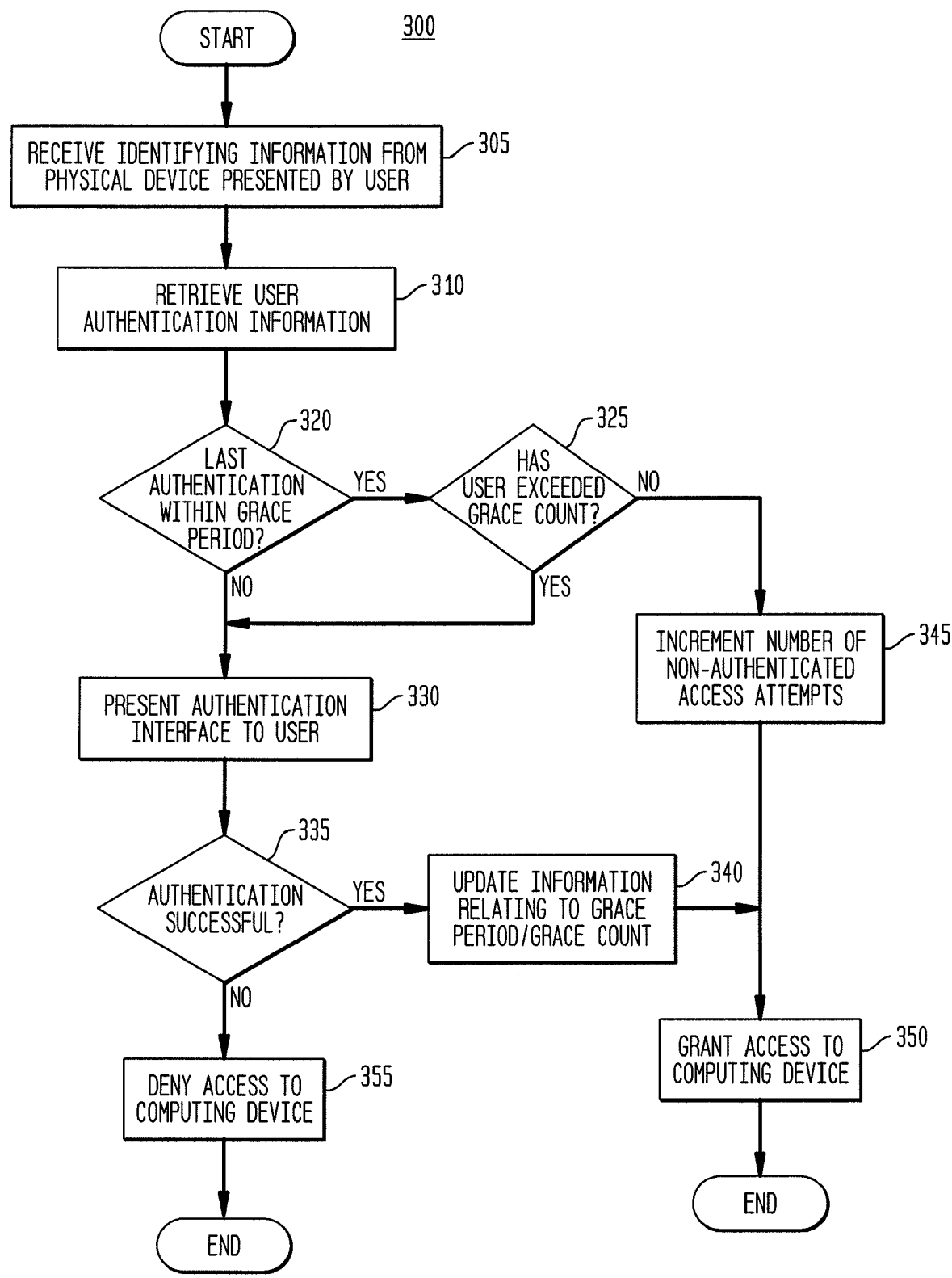
FIG. 3 is a flowchart depicting a process whereby a user may be granted access to at least one computing device, in accordance with one embodiment of the invention.

FIG. 3 depicts one example of a process 300 which may be performed by the computing environment (e.g., by the access control facility 115 in FIG. 1) to manage the granting of access to a user in accordance with one embodiment of the invention. It should be appreciated that this example is provided merely for illustrative purposes, and that the aspects of the present invention described herein are not limited to this particular implementation, as numerous other implementations are possible.

Initially, the system receives identifying information from a physical device presented by the user in act 305. For example, as described above in connection with the system 100 of FIG. 1, any of readers 105A-105n may receive identifying information from a passive proximity badge (or some other type of physical device) presented by the user and provide this information via a corresponding computing device 110 and network 112 to access control facility 115. Of course, the aspects of the present invention described in connection with FIG. 3 are not limited to being used with a system such as that shown in FIG. 1, and can be used with numerous other types of system configurations.

The process then proceeds to act 310, wherein the system employs the identifying information to retrieve user authentication information. The retrieved information can include information of many different types, as the present invention is not limited in this respect. For example, the retrieved information can include an identifier for the user, the time at which the user was last fully authenticated, the user's grace period, the user's grace count (described further below), the number of access attempts previously performed by the user since last providing credential information, etc. The retrieved information can be obtained in any suitable manner. For example, access control facility 115 (FIG. 1) may employ the identifying information provided in act 305 to perform a lookup of authentication datastore 120, although other implementations are possible.

The process then proceeds to act 320, wherein a determination is made as to whether the user's last full authentication occurred within the user's grace period. This can be done in any suitable manner. For example, access control facility 115 may employ information retrieved in act 310 to determine whether the difference between a current time (e.g., the time at which act 305 is performed) and the time at which the last authentication occurred is less than the user's grace period. It should be appreciated that this determination can also be done in other ways, as the invention is not limited to this particular implementation.

The grace period may be any suitable time period. For example, grace periods may be specific to each user, assigned to all users in a particular role and/or department, assigned to all users in an organization, or assigned in any other suitable manner. Further, a grace period need not run from the last full authentication by the user, as it may run from any suitable event, and may be suspended, altered or otherwise modified (e.g., by a system administrator) in any desired manner. For example, if it is determined that a security breach has occurred, a system administrator may temporarily suspend all user grace periods, such that all users must thereafter be fully authenticated.

If it is determined in act 320 that the user's last authentication was within the user's grace period, the process proceeds to act 325, wherein a determination is made as to whether the user has exceeded his or her grace count. This can be done in any suitable manner. For example, access control facility 115 may employ information retrieved in act 310 to determine whether the number of access attempts previously performed by the user since last providing credential information exceeds the user's grace count. Of course, this can be done in any of numerous ways, and is not limited to this or any particular implementation.

In one embodiment, a grace count specifies a maximum number of times a user may be granted access without providing credential information. For example, after providing credential information the first time, the user may be granted access by presenting only the physical device a maximum number of times before he/she must again provide credential information. Like the grace period, grace counts may be assigned to users in any suitable fashion (e.g., individually, by role, department or organization, and/or using any other suitable assignment scheme), and may be suspended, altered or otherwise modified as circumstances warrant (e.g., if a security breach or another event occurs). The embodiment of the invention that implements grace counts is not limited to any particular implementation, and it should be appreciated that a grace count is optional and need not be implemented in all embodiments.

If it is determined that the user's grace count has not been exceeded, the process proceeds to act 345, wherein the information recording the number of access attempts since providing the credential information is incremented. This can be done in any suitable fashion. For example, access control facility 115 may increment an indication of the number of non-authenticated access attempts in authentication datastore 120.

The process then proceeds to act 350, wherein the user is granted access to the computing device, and process 300 terminates.

If it is determined in act 320 that the user's last authentication was not within the grace period, or if it is determined in act 325 that the number of access attempts has exceeded the grace count, the process proceeds to act 330, wherein an authentication interface is presented to prompt the user to provide credential information.

The process then proceeds to act 335, wherein it is determined whether the user's authentication is successful. If not, access to the computing device is denied in act 355, whereupon process 300 ends. If the authentication is successful, the process proceeds to act 340, wherein information relating to the grace period and grace count are updated. This can be done in any suitable fashion. For example, authentication database 120 may be updated with an indication of the time of the authentication in act 330 to reset the grace period and/or the number of non-authenticated access attempts may be reset to zero to indicate that the user was authenticated.

Upon the completion of act 340, the process proceeds to act 350, wherein the user 1o is granted access to the computing device, and the process 300 terminates.

In accordance with one embodiment, aspects of the present invention may be employed in a computing environment wherein one or more user interface terminals (e.g., workstations) may be shared by multiple users at various times. As mentioned above, one example of such a shared computing environment is a healthcare environment 15 (e.g., a hospital), although numerous other shared computing environments are possible.

Some shared computing environments provide the ability for a particular user to lock a computing device (e.g., a workstation) to prevent other users from accessing the applications and/or data presented thereby from that workstation. The user may seek to lock the computing device for any number of reasons. For example, a user may be using a particular workstation and desire to walk away from it briefly while intending to return soon, and desire to maintain the applications and data on the computing device in the same state but to make the computer inaccessible to another user. In accordance with one embodiment, one or more of the aspects of the present invention described herein can be incorporated into a system that employs a locking capability.

In one embodiment, if the physical device (e.g., proximity badge) associated with the user that locked the workstation (e.g., user A) is presented, the system may ignore the action or process the action to determine whether to unlock the workstation. This processing can be done in any of numerous ways, as the invention is not limited in this respect. In accordance with one embodiment, the workstation may simply be unlocked if the physical device associated with the user who locked the workstation is presented. Alternatively, the presentation of the physical device may be treated like other attempts to access the workstation discussed above, and the physical device may be accepted to unlock the workstation only if the grace period for the user has not expired and/or the grace count has not been exceeded.

In accordance with one embodiment of the present invention, uses of the physical device (e.g., passive proximity badge) to unlock a workstation do not count towards the number of non-authenticated accesses tracked by the grace count, and the grace count is not checked to determine whether to provide an unlocking of the workstation access. However, it should be appreciated that the invention is not limited in this respect, and that an attempt to unlock a workstation may be treated as a non-authenticated access.

In accordance with one embodiment of the present invention, if one user (e.g., user A) is working on a workstation and another user (e.g., user B) seeks to access the workstation by presenting his/her physical device (e.g., passive proximity badge), no user change or dialog will be presented and the presentation of the physical device for the second user will essentially be ignored. However, it should be appreciated that the invention is not limited in this respect, and the presentation of the physical device by the second user can be treated differently in alternate embodiments (e.g., by crediting the new access attempt and processing it in any of the manners discussed above).

In accordance with one embodiment, a capability is provided that minimizes risks associated with the physical device being lost or stolen and used by one other than the rightful owner. For example, in accordance with one embodiment of the present invention, a capability is provided for a user to disable his/her physical device (e.g., proximity badge). For example, if a user discovers that his/her device has been lost or stolen, the user may access the computing environment (e.g., by providing credential information to authenticate the user's identity) and may disable the physical device so that any attempted access will be denied even if the access occurs before the expiration of any grace period and does not exceed any grace count. In accordance with another embodiment of the invention, when the device is disabled, any user session initiated by providing the physical device can be immediately terminated. In addition to providing the user with the capability to disable his/her device, such a capability can also be provided to a system administrator in accordance with one embodiment of the present invention.

In accordance with another embodiment of the present invention, a capability can be provided to monitor whether two users are logged into the computing environment simultaneously at multiple workstations using the same identity. This can be accomplished in any of numerous ways, as the aspect of the present invention that provides this capability is not limited to any particular implementation technique. This capability provides a safeguard in that if a user's physical device is lost or stolen and another user seeks access to the computing environment using that physical device simultaneously with the rightful owner accessing the computing environment using credential information, such an occurrence can be detected. In accordance with one embodiment of the present invention, if it is determined that a single user's identity has been used to log into multiple workstations at the same time, the physical device (e.g., proximity badge) associated with that user can be immediately revoked and any user session that was initiated based solely on the presentation of that device (i.e., without the user providing credential information) can be automatically terminated.

In accordance with one embodiment of the present invention, the enrollment of a physical device so that it can be recognized by the computing environment is limited to control by a system administrator, so that a user cannot self-enroll. However, it should be appreciated that the present invention is not limited in this respect, and that self-enrollment can be provided in alternate embodiments.

As discussed above, the aspects of the present invention described herein can be implemented on computing environments that take any suitable form, as the invention is not limited in this respect. The computing devices through which a user may gain access to the computing environment, as well as the portions of the computing environment on which the various processes described above can be implemented, can take any of numerous forms, as the embodiments of the invention described herein are not limited in this respect.

Figure 4:
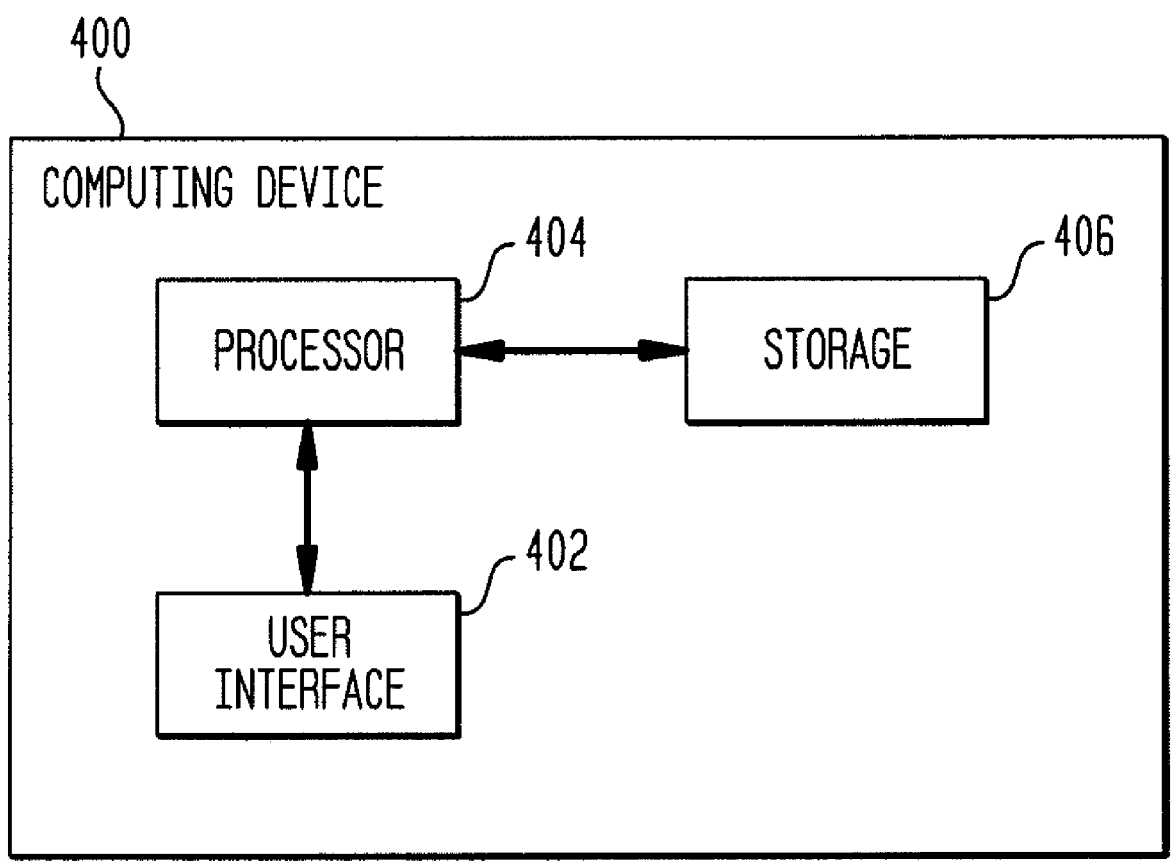
FIG. 4 is a block diagram depicting an exemplary computing device on which aspects of the invention may be implemented.

A simple illustration of a computing device 400 that can be used to serve as any of the computing devices through which a user may gain access to a computing environment, or to perform the processing of all or a portion of the various processes described above for implementing aspects of the present invention, is shown in FIG. 4. The computing device 400 comprises a user interface 402 that may be one or more suitable input/output device(s) for allowing a user to communicate with the computing device 400. The computing device further comprises a processor 404 and storage 406. The storage 406 can comprise any type of computer-readable medium for storing information readable by the processor 404 (e.g., volatile or non-volatile memory, disk storage, etc.) as the present invention is not limited to use with a computing device having any particular type of computer-readable medium for storing information. The processor 404 can be programmed to execute computer code (e.g., software and/or firmware) to implement any of the various functions described herein, and the computer code can be provided on the storage 406.

The above-described embodiments of the present invention can be implemented in any of numerous ways, for example, using hardware, software or a combination thereof. When implemented in software, the software code can be executed on any suitable processor (e.g., processor 403) or collection of processors, whether provided in a single computer (e.g., computing device 400) or distributed among multiple computers. It should be appreciated that any component or collection of components that perform the functions described above can be generically considered as one or more controllers that control the above-discussed function. The one or more controllers can be implemented in numerous ways, such as with dedicated hardware, or with general purpose hardware (e.g., one or more processors) programmed (e.g., using microcode and/or software) to perform the functions recited above.

As mentioned above, the embodiments described herein may be implemented using software executable on one or more processors. In this respect, it should be appreciated that one embodiment of the invention is directed to a computer-readable medium (or multiple computer-readable media) (e.g., a computer memory, one or more floppy disks, compact disks, optical disks, magnetic tapes, etc.) encoded with one or more programs that, when executed on one or more processors, perform methods that implement the various embodiments of the invention discussed above. The computer-readable medium or media can be transportable, such that the program or programs stored thereon can be loaded onto one or more processors to implement various aspects of the present invention as discussed above.

It should be understood that the term "program" is used herein in a generic sense to refer to any type of computer code or set of instructions that can be employed to program a processor to implement various aspects of the present invention as discussed above. Additionally, it should be appreciated that one or more computer programs that, when executed, perform methods of the present invention need not reside on a single processor, but may be distributed in a modular fashion amongst a number of different processors to implement various aspects of the present invention.

Various aspects of the present invention may be used alone, in combination, or in a variety of arrangements not specifically discussed above, and they are not limited to the details and arrangements of components set forth in the foregoing description or illustrated in the drawings. The invention is capable of being practiced or carried out in various ways. Accordingly, the foregoing description and drawings are by way of example only. The use of "including," "comprising," or "having," "containing," "involving," and variations thereof herein is meant to encompass the items listed thereafter and equivalents thereof, as well as additional items.

Having thus described several aspects of at least one embodiment of this invention, it is to be appreciated various alterations, modifications, and improvements will readily occur to those skilled in the art. Such alterations, modifications, and improvements are intended to be within the spirit and scope of the invention.

What is claimed is:

1. A method, performed by a user, of gaining access to at least one computing device, the method comprising acts of:
   (A) gaining access to the at least one computing device at a first time by providing credential information to the at least one computing device to authenticate the user's identity to the at least one computing device;
   (B) presenting to a first user interface for the at least one computing device a passive proximity badge comprising identifying information to demonstrate that the user authenticated by the credential information was in possession of the passive proximity badge at the first time; and
   (C) gaining access to the at least one computing device at a second time, subsequent to the first time, by presenting the passive proximity badge to the first user interface or a different user interface of the at least one computing device without providing the credential information to authenticate the user's identity to the at least one computing device at the second time, wherein the second time is subsequent to the first time by a period of time that is less than a grace period established by the at least one computing device to enable the user to regain access to the at least one computing device without providing the credential information to authenticate the user's identity to the at least one computing device;

wherein the at least one computing device comprises a computer system comprising a plurality of computers coupled via at least one communication medium, wherein the computer system comprises a plurality of user interfaces organized into a plurality of groups, and wherein one of the plurality of user interfaces associated with a first group has a grace period established which is different than a grace period established for another of the plurality of user interfaces associated with a second group.

2. The method of claim 1, wherein the credential information provided in the act (A) comprises a user identifier and a password.

3. The method of claim 1, wherein the credential information provided in the act (A) comprises biometric information about the user.

4. The method of claim 1, further comprising an act of:
(D) gaining access to the at least one computing device at a third time that is subsequent to the second time by greater than the grace period by providing the credential information to the at least one computing device to authenticate the user's identity to the at least one computing device.

5. The method of claim 1, wherein the at least one computing device is part of a computing system for a healthcare organization and the user is a healthcare provider.

6. The method of claim 1, wherein the at least one computing device comprises a computer system comprising a plurality of computers coupled via at least one communication medium, the plurality of computers comprising at least a first computer and a second computer, wherein the act (A) comprises an act of gaining access to the computer system via the first computer, and wherein the act (C) comprises gaining access to the computer system via the second computer.

7. The method of claim 1, wherein the access to the at least one computing device comprises a first session of the user using the at least one computing device, and wherein the act (B) comprises an act of presenting the at least one physical device to the at least one computing device while gaining access to the at least one computing device at the first time and/or during the first session after the user's identify has been authenticated.

8. The method of claim 1, wherein the act (C) comprises gaining access to the at least one computing device at the second time by presenting the passive proximity badge to a second user interface of the at least one computing device that is different from the first user interface.

9. The method of claim 8, wherein the at least one computing device comprises a computer system comprising a plurality of computers coupled via at least one communication medium, the plurality of computers comprising at least a first computer and a second computer;
wherein the first user interface is associated with the first computer so that the act (A) comprises an act of gaining access to the computer system via the first computer; and
wherein the second user interface is associated with the second computer so that the act (C) comprises gaining access to the computer system via the second computer.

10. The method of claim 1, wherein the act (C) comprises gaining access to the at least one computing device at the second time by presenting the passive proximity badge to the first user interface.

11. The method of claim 1, further comprising an act, performed before the act (C), of presenting the passive proximity badge, comprising identifying information, to the first user interface to associate the passive proximity badge with the user authenticated by the credential information.

\* \* \* \* \*